United States Patent
Davis

(10) Patent No.: US 7,105,501 B2
(45) Date of Patent: Sep. 12, 2006

(54) COMPOSITIONS WITH VASCULAR DAMAGING ACTIVITY

(75) Inventor: Peter David Davis, Watlington (GB)

(73) Assignee: Angiogene Pharmaceuticals Ltd., Watlington (GB)

(*) Notice: Subject to any disclaimer, the term of this patent is extended or adjusted under 35 U.S.C. 154(b) by 0 days.

(21) Appl. No.: 10/367,606

(22) Filed: Feb. 14, 2003

(65) Prior Publication Data

US 2003/0181424 A1 Sep. 25, 2003

Related U.S. Application Data

(63) Continuation of application No. PCT/GB01/03668, filed on Aug. 15, 2001.

(30) Foreign Application Priority Data

Aug. 15, 2000 (GB) .............................. 0019944

(51) Int. Cl.
*A61K 31/66* (2006.01)
*C07F 9/02* (2006.01)

(52) U.S. Cl. .................. 514/130; 558/197; 558/210

(58) Field of Classification Search ................ 558/197, 558/210; 514/130; 424/1.11
See application file for complete search history.

(56) References Cited

U.S. PATENT DOCUMENTS

| | | | | |
|---|---|---|---|---|
| 4,996,237 A | * | 2/1991 | Pettit et al. ................. | 514/720 |
| 5,430,062 A | * | 7/1995 | Cushman et al. ........... | 514/646 |
| 5,554,638 A | * | 9/1996 | Dewhirst et al. ........... | 514/398 |
| 5,561,122 A | | 10/1996 | Pettit ........................... | 514/130 |
| 6,670,334 B1 | * | 12/2003 | Venit et al. .................. | 514/130 |

FOREIGN PATENT DOCUMENTS

| WO | 92/16486 | * | 10/1992 |
|---|---|---|---|
| WO | 9935150 | | 7/1999 |
| WO | 00/48606 | | 8/2000 |
| WO | 01/12579 | | 2/2001 |

OTHER PUBLICATIONS

Pettite George, et al., Anti–neoplastic agents 463. Synthesis of Combretastatin A–3 diphosphate prodrugs, Anti–Cancer Drug Design (2001), Volume Date 2000, 15(6), 397–403.*
Tozer et al., Combrestastatin A–4 Phosphate as a Tumor Vascular–Targeting Agent: Early Effects in Tumors and Normal Tissues, "Cancer Research", 59, pp. 1626–16234, 1999.*
Bedford, S. B. et al. "Synthesis of Water–Soluble Prodrugs of the Cytotoxic Agent Combretastatin A4." Bioorganic & Medicinal Chemistry Letters, vol. 6, No. 2 (1996) pp 157–160.
Tozer, G. M., et al. "Combretastatin A–4 Phosphate as a Tumor Vascular–Targeting Agent . . . " Cancer Research, vol. 59, No. 7 (1999) pp. 1626–1634.
Pettit, G. R., et al. "Antineoplastic agents 429. Syntheses of the combretastatin A–1 and combretastatin B–1 prodrugs." Anti–Cancer Drug Design, vol. 15, No. 3 (2000) pp. 203–216.

* cited by examiner

*Primary Examiner*—Johann Richter
*Assistant Examiner*—Ebenezer Sackey
(74) *Attorney, Agent, or Firm*—Ladas & Parry LLP

(57) ABSTRACT

Compositions for the inhibition of the formation of new vaculature by angiogenesis are provided as in compounds which are salts comprising as an acidic component a compound of formula (1) wherein: $R^1$, $R^2$ and $R^3$ are each independently alkyl, $R^4$ is alkoxy, haloalkoxy, alkyl, haloalkyl, alkenyl, alkynyl, alkylthio, alkylsulphinyl, alkylsulphonyl, hydroxy or halo, $R^5$ is hydrogen, alkoxy, alkyl, alkylthio, hydroxy, phosphate or halo, and, as the basic component, a compound selected from the group consisting of (2) a compound of formula (2) wherein $R^6$ is hydrogen or alkyl $R^7$ is alkyl, alkylamino, dialkylamino, nitroamino, hydrazine, mercapto or alkylthio X is $CH_2$, $CH_2CH_2$, $CH_2S$, $CH_2CH_2S$ Y is NH or S or a compound of formula (3) wherein $R^8$ is alkyl or aminoalkyl $R^9$ is hydrogen, alkyl or optionally substituted phenyl or, a compound of formula (4) wherein Z is O, S, $CH2$, $CHR13$ or a bond $R^{10}$, $R^{11}$, $R^{12}$ and $R^{13}$ are each independently alkyl or hydrogen or, a compound of formula (5) wherein $R^{14}$ is alkyl and the pharmaceutically acceptable solvates and hydrates thereof.

14 Claims, No Drawings

COMPOSITIONS WITH VASCULAR DAMAGING ACTIVITY

This application is a continuation of PCT/GB01/03668 filed on Aug. 15, 2001.

The present invention relates to compounds for the treatments of diseases involving active angiogenesis and which are new vascular damaging agents.

Formation of new vasculature by angiogenesis is a key pathological feature of several diseases (J Folkman, New England Journal of Medicine 333, 1757–1763 (1995)). For example, for a solid tumour to grow it must develop its own blood supply upon which it depends critically for the provision of oxygen and nutrients; if this blood supply is mechanically shut off the tumour undergoes necrotic death. Neovascularisation is also a clinical feature of skin lesions in psoriasis, of the invasive pannus in the joints of rheumatoid arthritis patients and of atherosclerotic plaques. Retinal neovascularisation is pathological in macular degeneration and in diabetic retinopathy. In all these diseases reversal of neovascularisation by damaging the newly-formed vascular endothelium is expected to have a beneficial therapeutic effect.

Compounds able to damage neovasculature have advantages in the treatment of disease. For example, attacking tumour vasculature has several important advantages over a direct attack on the tumour. In particular the endothelial cells of tumour vasculature are more genetically stable than those of the tumour itself and are therefore less likely to become resistant to the damaging agent. Thus a major problem in conventional anti-tumour chemotherapy, that of drug resistance, is circumvented by this approach. Furthermore, since the endothelial cells of the tumour vasculature, unlike the tumour cells themselves, are similar between different solid tumour types, vascular damaging agents are able to attack a wide range of tumour types.

Certain chemical compounds have been shown to have vascular damaging activity against the newly formed endothelium of solid tumours. These agents include, for example, combretastatin A1 and combretastatin A4 (D. J. Chaplin et al., British J. Cancer 27, S86–S88, 1996), combretastatin A4 phosphate (Dark et al., Cancer Research 57, 1829–1834, 1997), combretastatin A1 phosphate (Holwell et al. Proc. Amer. Assoc. Cancer Res. 41, 1363, 2000), AC7700 (Hori et al. Jpn. J. Cancer Res. 90, 1026–1038, 1999), colchinol derivatives (Davis et al., WO 98/01977 and Davis et al. WO00/40529), benzimidazole derivatives (Davis, WO00/41669), the flavone acetic acids, for example 5,6-dimethylxanthenone acetic acid (Zwi, Pathology, 26, 161–9, 1994) and colchicine (Baguley et al. Eur J Cancer 27, 482–7, 1991). However some tumours are relatively resistant to these agents. The combination of a vascular damaging agent and inhibitors of the formation or action of nitric oxide in a mammalian system have proved to be superior in some instances (Angiogene Pharmaceuticals Limited WO 00/48591).

Tozer et al (Cancer Research 59, 1626–1634, 1999) have described the activity of combretastain A4 phosphate in the rat P22 tumour model, which is sensitive to this agent. These authors also demonstrated an enhancing effect of L-NAME on the activity of combretastatin A4 phosphate and ascribed the enhancement to inhibition of nitric oxide production. However it is not apparent from these studies that this is a general effect of inhibition of nitric oxide production. In these studies the L-NAME was given in the drinking water while the combretastatin A4 phosphate was given as an intraperitoneal injection.

Various salts of combretastatin A4 have been described for example the disodium salt, the monosodium salt, the cesium salt, the calcium salt, the lithium salt, the magnesium salt, the zinc salt, the salt formed with imidazole, the salt formed with morpholine, the salt formed with piperazine, the salt formed with piperidine, the salt formed with pyrazole, the salt formed with pyridine, the salt formed with adenosine, the salt formed with cinchonine, the salt formed with quinine, the salt formed with quinidine, the salt formed with glucosamine, the salt formed with tetracycline and the salt formed with verapamil (Pettit et al. Anti-Cancer Drug Design 13, 981–993, 1998). None of these has been shown to have significant therapeutic advantage over the parent phosphate.

We have found a series of novel salts with vascular damaging activity. These salts have potent vascular damaging activity and are active against tumours which are resistant to vascular damaging agents such as the combretastatins. These compounds specifically damage newly-formed vascular endothelium, especially that associated with solid tumours, without affecting the normal, established vascular endothelium of the host species. Such compounds are of use in the prophylaxis and treatment of cancers involving solid tumours and in other diseases where there is inappropriate formation of new vasculature such as diabetic retinopathy, psoriasis, rheumatoid arthritis, macular degeneration and the formation of atherosclerotic plaques. The salts are stable, soluble in aqueous media and conveniently provide a dose of a vascular damaging agent along with a dose of a nitric oxide synthase inhibitor wherein the two agents are provided in an advantageous ratio. The salts show improved vascular-damaging properties.

Thus according to one aspect of the invention we provide a salt comprising, as the acidic component, a compound of formula (1)

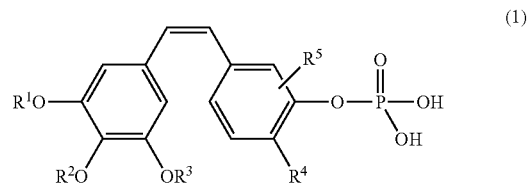

(1)

Wherein:
$R^1$, $R^2$ and $R^3$ are each independently alkyl,
$R^4$ is alkoxy, haloalkoxy, alkyl, haloalkyl, alkenyl, alkynyl, alkylthio, alkylsulphinyl, alkylsulphonyl, hydroxy or halo,
$R^5$ is hydrogen, alkoxy, alkyl, alkylthio, hydroxy, phosphate or halo,
and, as the basic component, a compound of formula (2)

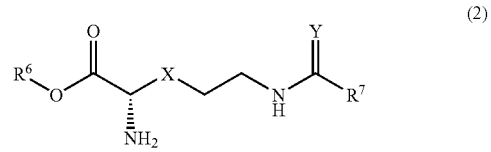

(2)

Wherein
$R^6$ is hydrogen or alkyl
$R^7$ is alkyl, alkylamino, dialkylamino, nitroamino, hydrazine, mercapto or alkylthio
X is $CH_2$, $CH_2CH_2$, $CH_2S$, $CH_2CH_2S$
Y is NH or S or, as the basic component, a compound of formula (3)

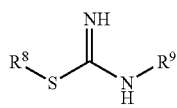

(3)

Wherein
R[8] is alkyl or aminoalkyl
R[9] is hydrogen, alkyl or optionally substituted phenyl
or, as the basic component, a compound of formula (4)

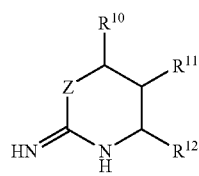

(4)

Wherein
Z is O, S, CH2, CHR13 or a bond
R[10], R[11], R[12] and R[13] are each independently alkyl or hydrogen
or, as the basic component, a compound of formula (5)

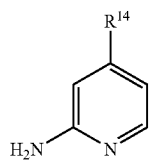

(5)

Wherein
R[14] is alkyl
and the pharmaceutically acceptable solvates and hydrates thereof.

The molar ratio of acidic to basic components in salts of the invention is preferably about 1:1 or about 1:2.

As used herein the term "alkyl", alone or in combinations, means a straight or branched-chain alkyl group containing from one to seven, preferably a maximum of five, carbon atoms such as methyl, ethyl, propyl, isopropyl, butyl, sec-butyl, t-butyl and pentyl. Examples of alkoxy groups are methoxy, ethoxy, propoxy, isopropoxy, butoxy and t-butoxy.

The term "halogen" means fluorine, chlorine, bromine or iodine.

An alkenyl group may be for example an olefinic group containing from two to seven carbon atoms for example methylene, ethylene, n-propylene, i-propylene, n-butylene, i-butylene, s-butylene and t-butylene. An alkynyl group may be for example an ethynyl, propynyl or butynyl group.

Optional substituents which may be present on a phenyl group may include, for example, one or more substituents selected from alkyl, haloalkyl, alkoxy, halo alkoxy, phenoxy, benzyloxy, carboxy, alkoxycarbonyl, halo and nitro.

Those skilled in the art will recognise that compounds of formulae (2), (3), (4) and (5) can exist in more than one tautomeric form and the invention is intended to encompass all such tautomeric forms.

Compounds of the invention can be prepared by any process known to a person skilled in the art. The salts can be prepared by standard techniques, for example by the addition of about one to about two molar equivalents of a compound of formula (2), (3), (4) or (5) in an appropriate solvent to a compound of formula (1) in an appropriate solvent. Appropriate solvents include, for example, water, alcohols such as, for example, methanol, ethanol or isopropanol, chlorinated solvents, for example dichloromethane or chloroform, ketone solvents such as acetone or methyl ethyl ketone, ether solvents such as diethyl ether, methyl t-butyl ether, dioxane or tetrahydrofuran and nitrites such as acetonitrile and mixtures thereof. The acidic and basic components of the salt may be dissolved in the same solvent (or solvent mixture) or in a different solvent (or solvent mixture) provided the solvents are miscible. The salts can be isolated by evaporation, crystallisation, freeze-drying or precipitation and may be purified by recrystallisation or reprecipitation.

Compounds of formulae (1) can be prepared by a number of processes as generally described hereinbelow and more specifically in the Examples hereinafter. In the general preparations described below it may be necessary to employ protecting groups which are then removed during the final stages of the synthesis. The appropriate use of such protecting groups and processes for their removal will be readily apparent to those skilled in the art. In the following process description, the symbols R[1], R[2], R[3], R[4] and R[5], when used in the formulae depicted are to be understood to represent those groups described above in relation to formula (1) unless otherwise indicated In one general example compounds of formula (1) can be prepared by phosphorylation of phenols of formula (6) by treatment with for example di-tert-butyl diethylphosphoramidite in the presence of a suitable catalyst for example tetrazole or in a solvent such as an ether solvent for example tetrahydrofuran at a temperature in the range −40 to 40° C., conveniently at or near room temperature, followed by treatment with an oxidising agent for example 3-chloroperoxy benzoic acid or magnesium monoperoxyphthalate at a temperature in the range −78° C. to 40° C. preferably −65 to −10° C. The resulting intermediate phosphate triester is treated with an acid for example trifluoroacetic acid in a solvent such as a chlorinated solvent e.g. dichloromethane at a temperature in the range −30 to 40° C. conveniently at or near 0° C. to give the compound of formula (1).

Compounds of formula (6) can be prepared by Wittig olefin synthesis involving reaction of a phosphonium salt of formula (7) with a strong base, for example an alkyllithium such as n-butyllithium or t-butyllithium or a metal hydride such as sodium hydride in a solvent such as an ether solvent for example diethyl ether or tetrahydrofuran or in a solvent such as a hydrocarbon solvent for example toluene at a temperature of between about −100° C. to about 30° C. followed by treatment with an aldehyde of formula (8) in which G is a protecting group, to give an intermediate of formula (9). The synthesis of compounds of formula (6) is then completed by removal of the group G. Suitable protecting groups G include trialkylsilyl, for example t-butyldimethylsilyl, and allyl. Where G is a triallylsilyl group it may be removed, for example, by treatment with a quaternary ammonium fluoride such as tetrabutylammonium fluoride in an ether solvent such as tetrahydrofuran at a temperature of about −30° C. to about 40° C. conveniently at or near ambient temperature. Where G is an allyl group it may be removed for example by treatment with a palladium (0) complex such as tetrakis(triphenylphosphine)Pd(0) in a solvent such as a chlorinated solvent, for example dichloromethane, at a temperature of about −40° C. to about 40° C. conveniently at or near ambient temperature, in the presence of an allyl scavenger such as morpholine.

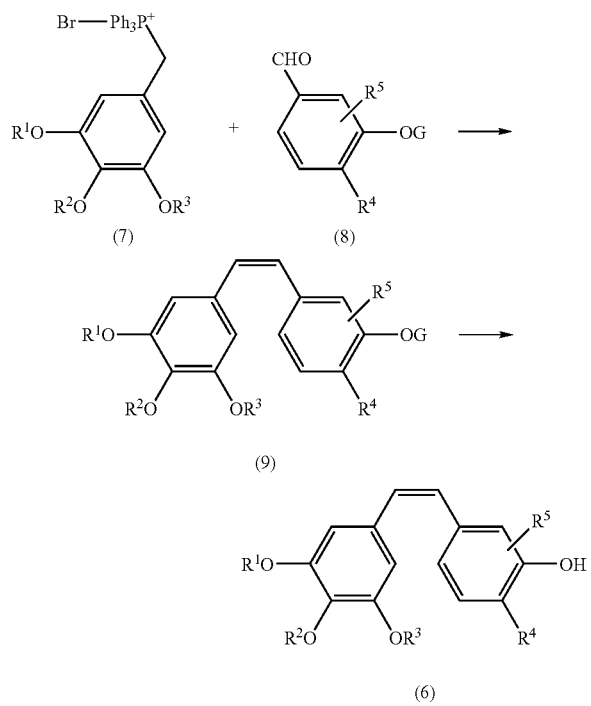

(7) (8)

(9)

(6)

Aldehydes of formula (8) can be prepared by any process known to a person skilled in the art. In one general example an aldehyde of formula (8) can be prepared from an alcohol of formula (10) by oxidation with a suitable oxidising agent. Suitable oxidising agents include the Dess-Martin reagent and manganese dioxide. Alcohols of formula (10) can be prepared by application of standard methods of organic synthesis including the selective protection of phenols of formula (11). Where the protecting group G is a trialkylsilyl group, for example t-butyldimethylsilyl, alcohols of formula (10) may be prepared, for example, by treatment of a phenol of formula (11) with a strong base, for example an alkyllithium such as n-butyllithium or t-butyllithium or a metal hydride such as sodium hydride in a solvent such as an ether solvent for example diethyl ether or tetrahydrofuran or in a solvent such as a hydrocarbon solvent for example toluene at a temperature of between about −100° C. to about 40° C. followed by treatment with tert-butylchlorodimethylsilane.

Phenols of formula (11) are either known or may be prepared from known compounds using standard methods of organic synthesis.

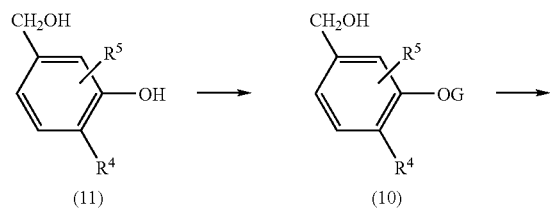

(11) (10)

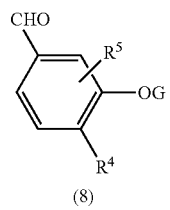

(8)

Compounds of formulae (2), (3), (4) and (5) are either known or can be prepared by methods analogous to those described in the literature.

Compounds according to the invention are able to destroy tumour vasculature and vasculature that has been newly formed. The ability of the compounds to act in this way may be determined by the tests described hereinafter.

The compounds according to the invention are thus of particular use in the prophylaxis and treatment of cancers involving solid tumours and in the prophylaxis and treatment of diseases where inappropriate angiogenesis occurs such as diabetic retinopathy, psoriasis, rheumatoid arthritis, atherosclerosis and macular degeneration.

The compounds of the invention may be administered as a sole therapy or in combination with other treatments. For the treatment of solid tumours compounds of the invention may be administered in combination with radiotherapy or in combination with other anti-tumour substances for example those selected from mitotic inhibitors, for example vinblastine, vincristine, vinorelbine, paclitaxel and docetaxel; platinum derivatives for example cisplatin and carboplatin; alkylating agents, for example melphalan, chlorambucil, busulphan, ifosfamide and cyclophosphamide; antimetabolites, for example methotrexate, 5-fluorouracil, cytosine arabinoside, gemcitabine and hydroxyurea; antitumour antibiotics for example bleomycin, doxorubicin, daunomycin, epirubicin, idarubicin, mitomycin-C, dactinomycin and mithramycin, enzymes, for example aspariginase; topoisomerase inhibitors for example etoposide, teniposide, topotecan and irinotecan; thymidylate synthase inhibitors for example raltitrexed; biological response modifiers for example interferon; antibodies for example edrecolomab and trastuzumab; anti-hormones for example tamoxifen, toremifene, raloxifene, droloxifene, iodoxyfene, anastrozole, letrazole, vorazole, exemestane, flutamide, nilutamide and bicalutamide, anti-growth factor compounds for example EGFr tyrosine kinase inhibitors VEGFr kinase inhibitors and PDGFr tyrosine kinase inhibitors, and anti-angiogenesis agents such as angiostatin, endostatin and thalidomide. Such combination treatment may involve simultaneous or sequential application of the individual components of the treatment.

For the prophylaxis and treatment of disease the compounds according to the invention may be administered as pharmaceutical compositions selected with regard to the intended route of administration and standard pharmaceutical practice. Such pharmaceutical compositions may take a form suitable for oral, buccal, nasal, topical, rectal or parenteral administration and may be prepared in a conventional manner using conventional excipients. For example for oral administration the pharmaceutical compositions may take the form of tablets or capsules. For nasal administration or administration by inhalation the compounds may be conveniently delivered as a powder or in solution. Topical administration may be as an ointment or cream and rectal administration may be as a suppository. For parenteral injection (including intravenous, subcutaneous, intramuscular, intravascular or infusion) the composition may take the form of, for example, a sterile solution, suspension or emulsion.

The dose of a compound of the invention required for the prophylaxis or treatment of a particular condition will vary depending on the compound chosen, the route of administration, the form and severity of the condition and whether the compound is to be administered alone or in combination with another drug. Thus the precise dose will be determined by the administering physician but in general daily dosages may be in the range 0.001 to 100 mg/kg preferably 0.1 to 10 mg/kg.

Biological Activity

The following tests were used to demonstrate the activity of compounds according to the invention.

Activity Against Tumour Vasculature Measured by Fluorescent Dye.

Tumour functional vascular volume in CaNT tumour-bearing mice was measured using the fluorescent dye Hoechst 33342 according to the method of Smith et al (Brit J Cancer 57, 247–253, 1988). At least three animals were used in control and treated groups. The fluorescent dye was dissolved in saline at 6.25 mg/ml and injected intravenously at 10 mg/kg 24 hours after drug treatment. One minute later, animals were killed and tumours excised and frozen; 10 μm sections were cut at 3 different levels and observed under UV illumination using an Olympus microscope equipped with epifluorescence. Blood vessels were identified by their fluorescent outlines and vascular volume was quantified using a point scoring system based on that described by Chalkley, (J Natl Cancer Inst, 4, 47–53, 1943). All estimates were based on counting a minimum of 100 fields from sections cut at the 3 different levels. The salts of the invention were more efficacious than their dihydrogen phosphate parent compounds.

| Compound | Dose (mg/kg) | % Reduction in Vascular Volume |
| --- | --- | --- |
| Example 1 | 50 | 78 |
| Example 2 | 50 | 42 |
| Example 5 | 50 | 86 |
| Combretastatin A4 phosphate | 100 | 26 |
| (Z)-2-methyl-5-[2-(3,4-,5-trimethoxyphenyl)ethenyl]phenyl dihydrogen phosphate | 100 | 28 |

Induction of Tumour Necrosis

Mice bearing either CaNT or SaS tumours were treated with the test compound and tumours excised after 24 h, fixed in formalin, embedded in paraffin, sectioned and stained with haematoxylin and eosin. Sections were scored based on the estimated area of necrosis as follows:

| % necrosis | score |
| --- | --- |
| 0–10 | 1 |
| 11–20 | 2 |
| 21–30 | 3 |
| 31–40 | 4 |
| 41–50 | 5 |
| 51–60 | 6 |
| 61–70 | 7 |

-continued

| % necrosis | score |
| --- | --- |
| 71–80 | 8 |
| 81–90 | 9 |
| 91–100 | 10 |

Control tumours had mean scores of 2.0 (CaNT) and 1.0 (SaS). The salts of the invention were more efficacious than their dihydrogen phosphate parent compounds.

| Compound | Tumour | Dose (mg/kg) | Score |
| --- | --- | --- | --- |
| Example 1 | CaNT | 50 | 8.7 |
| Example 2 | CaNT | 50 | 8.7 |
| Example 5 | CaNT | 50 | 10.0 |
| Combretastatin A4 phosphate | CaNT | 100 | 5.0 |
| (Z)-2-methyl-5-[2-(3,4-,5-trimethoxyphenyl)ethenyl]phenyl dihydrogen phosphate | CaNT | 100 | 5.3 |
| Example 1 | SaS | 300 | 7.0 |
| Example 2 | SaS | 100 | 7.7 |
| Combretastatin A4 phosphate | SaS | 500 | 1.4 |

The following non-limiting Example illustrates the invention:

EXAMPLE 1

(Z)-2-methoxy-5-[2-(3,4,5-trimethoxyphenyl)ethenyl] phenyl di(1-methoxycarbonyl-4-N'-nitroguanidinobutylammonium) phosphate A mixture of combretastatin A4 phosphate (23 mg) and L-N$^G$-nitroarginine methyl ester (L-NAME, 27 mg) was dissolved in water, stirred 18 h and freeze-dried to produce a white solid (50 mg) of melting point 117–121° C.

The following were prepared in an analogous fashion to Example 1:

EXAMPLE 2

(Z)-2-methyl-5-[2-(3,4,5-trimethoxyphenyl)ethenyl]phenyl (1-carboxy-4-N'-nitroguanidinobutylammonium) hydrogen phosphate From (Z)-2-methyl-5-[2-(3,4-,5-trimethoxyphenyl) ethenyl]phenyl dihydrogen phosphate (151 mg) and L-N$^G$-nitroarginine(87 mg) there was obtained a white solid of melting point 191–194° C.

EXAMPLE 3

(Z)-2-methyl-5-[2-(3,4,5-trimethoxyphenyl)ethenyl]phenyl (1-methoxycarbonyl-4-N'-nitroguanidinobutylammonium) hydrogen phosphate From (Z)-2-methyl-5-[2-(3,4,5-trimethoxyphenyl) ethenyl]phenyl dihydrogen phosphate (41 mg) and L-N$^G$-nitroarginine methyl ester (25 mg) there was obtained a white solid of melting point 89–91° C.

EXAMPLE 4

(Z)-2-methyl-5-[2-(3,4,5-trimethoxyphenyl)ethenyl]phenyl di(1-methoxycarbonyl-4-N'-nitroguanidinobutylammonium) phosphate From (Z)-2-methyl-5-[2-(3,4,5-trimethoxyphenyl) ethenyl]phenyl dihydrogen phosphate (41 mg) and L-N$^G$-nitroarginine methyl ester (50 mg) there was obtained a white solid of melting point 90–92° C.

EXAMPLE 5

(Z)-2-methyl-5-[2-(3,4,5-trimethoxyphenyl)ethenyl]phenyl (1-methoxycarbonyl-4-N'-nitroguanidinobutylammonium) hydrogen phosphate From (Z)-2-methyl-5-[2-(3,4,5-trimethoxyphenyl) ethenyl]phenyl dihydrogen phosphate (114 mg) and 2-amino-5,6-dihydro-6-methyl-4H-1,3-thiazine (50 mg) there was obtained a white solid of melting point 116–117° C.

I claim:

1. A salt comprising, as the acidic component, a compound of formula (1)

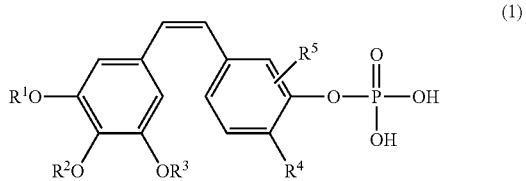

(1)

wherein:

R¹, R² and R³ are each independently alkyl,
R⁴ is alkoxy,
R⁵ is hydrogen, or alkyl, and, as the basic component, and a compound of formula (2)

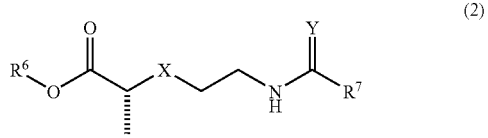

(2)

wherein:

R⁶ is hydrogen or alkyl,
R⁷ is nitroamino,
X is $CH_2$, or $CH_2CH_2$,
Y is NH, or the pharmaceutically acceptable solvates and hydrates thereof.

2. A compound according to claim 1 in which the molar ratio of acidic to basic components is 1:1 or 1:2.

3. A compound according to claim 1 which is (Z)-2-methoxy-5-[2-(3,4,5-trimethoxyphenyl)ethenyl]phenyl di(1-methoxycarbonyl-4-N'nitroguanidinobutylammonium) phosphate.

4. A compound according to claim 1 which is (Z)-2-methyl-5-[2-(3,4,5-trimethoxyphenyl)ethenyl]phenyl (1-carboxy-4-N'-nitroguanidinobutylammonium) hydrogen phosphate.

5. A compound according to claim 1 which is (Z)-2-methyl-5-[2-(3,4,5-trimethoxyphenyl)ethenyl]phenyl (1-methoxycarbonyl-4-N'-nitroguanidinobutylammonium) hydrogen phosphate.

6. A compound according to claim 1 which is (Z)-2-methyl-5-[2-(3,4,5-trimethoxyphenyl)ethenyl]phenyl di(1-methoxycarbonyl-4-N'-nitroguanidinobutylammonium) phosphate.

7. A compound according to claim 1 which is a reaction product of (Z)-2-methyl-5-[2-(3,4,5-trimethoxyphenyl) ethenyl]phenyl dihydrogen phosphate and 2-amino-5,6-dihydro-6-methol-4H-1,3-thiazine.

8. A composition for the treatment of a disease involving active angiogenesis which comprises a composition containing as active agent a vascular damaging agent which is a compound according to claim 1.

9. A method of treatment for a mammal having a disease involving active angiogenesis said method comprising administration of a vascular damaging agent characterised in that the vascular damaging agent is a compound according to claim 1.

10. A method according to claim 9 wherein the disease is selected from the group consisting of diabetic retinopathy, psoriasis, rheumatoid arthritis, atherosclerosis and macular degeneration.

11. A method of treatment of tumour vasculature comprising the administration of a vascular damaging agent selected from the group consisting of (Z)-2-methoxy-5-[2-(3,4,5-trimethoxyphenyl)ethenyl]phenyl di(1-methoxycarbonyl-4-N'-nitroguanidinobutylammonium) phosphate, (Z)-2-methyl-5-[2-(3,4,5-trimethoxyphenyl) ethenyl]phenyl (1-carboxy-4-N'-nitroguanidinobutylammonium) hydrogen phosphate, (Z)-2-methyl-5-[2-(3,4,5-trimethoxyphenyl)ethenyl]phenyl (1-methoxycarbonyl-4-N'-nitroguanidinobutylammonium) hydrogen phosphate, (Z)-2-methyl-5-[2-(3,4,5-trimethoxyphenyl)ethenyl]phenyl (1-methoxycarbonyl-4-N'-nitroguanidinobutylammonium hydrogen phosphate, and (Z)-2-methyl-5-[2-(3,4,5-trimethoxyphenyl)ethenyl]phenyl (1-methoxycarbonyl-4-N'-nitroguanidinobutylammonium) hydrogen phosphate.

12. A method according to claim 11 wherein the vasculature is associated with a solid tumour.

13. A method according to claim 11 wherein the vascular damaging agent is administered in a dosage of 0.1 to 10 mg/kg.

14. A method according to claim 11 wherein said vascular damaging agent is administered in a combination therapy involving treatment selected from the group consisting of radiotherapy and administration of other anti-tumour substances.

* * * * *

UNITED STATES PATENT AND TRADEMARK OFFICE
CERTIFICATE OF CORRECTION

PATENT NO.       : 7,105,501 B2                                             Page 1 of 1
APPLICATION NO.  : 10/367606
DATED            : September 12, 2006
INVENTOR(S)      : Peter David Davis It is certified that error appears in the above-identified patent and that said Letters Patent is hereby corrected as shown below:

Column 9, line 30, formula (2).

" 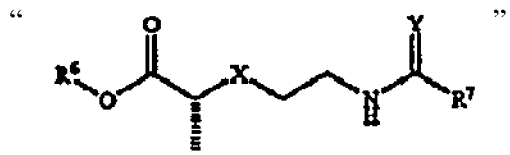 "

should read --

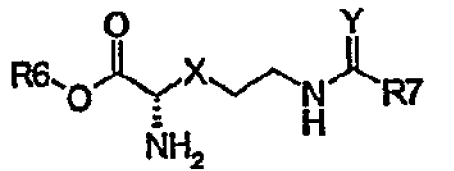

--.

Signed and Sealed this

Fourth Day of September, 2007

JON W. DUDAS
*Director of the United States Patent and Trademark Office*